United States Patent
Miskie

(10) Patent No.: US 6,679,867 B2
(45) Date of Patent: Jan. 20, 2004

(54) MALE INCONTINENCE DEVICE

(75) Inventor: John D. Miskie, Reading, PA (US)

(73) Assignee: Arcus Medical, LLC, Charlotte, NC (US)

(*) Notice: Subject to any disclaimer, the term of this patent is extended or adjusted under 35 U.S.C. 154(b) by 88 days.

(21) Appl. No.: 09/901,325

(22) Filed: Jul. 9, 2001

(65) Prior Publication Data

US 2002/0007160 A1 Jan. 17, 2002

Related U.S. Application Data

(60) Provisional application No. 60/217,434, filed on Jul. 10, 2000.

(51) Int. Cl.[7] .................................................. A61F 5/44
(52) U.S. Cl. .................... 604/349; 604/350; 604/323; 604/353
(58) Field of Search ................................ 604/349, 350, 604/323, 353

(56) References Cited

U.S. PATENT DOCUMENTS

| | | |
|---|---|---|
| 3,604,424 A | 9/1971 | Windom |
| 3,626,941 A | 12/1971 | Webb |
| 3,651,810 A | 3/1972 | Ormerod |
| 3,999,550 A | 12/1976 | Martin |
| 4,020,843 A | 5/1977 | Kanall |
| 4,022,213 A | 5/1977 | Stein |
| 4,187,851 A | 2/1980 | Hauser |
| 4,239,044 A | 12/1980 | Pavlinch |
| 4,387,726 A | 6/1983 | Denard |
| 4,626,250 A | 12/1986 | Schneider |
| 4,769,020 A | 9/1988 | Eaton |
| 4,894,059 A | 1/1990 | Larsen et al. |
| RE33,206 E | 5/1990 | Conway et al. |
| 4,994,051 A | 2/1991 | Walsh |
| 5,059,190 A | 10/1991 | Novak |
| 5,084,037 A | 1/1992 | Barnett |
| 5,211,640 A | 5/1993 | Wendler |
| 5,380,312 A | 1/1995 | Goulter |
| 5,478,334 A | 12/1995 | Bernstein |
| 5,531,725 A | 7/1996 | Steer |
| 5,618,277 A | 4/1997 | Goulter |
| 5,630,429 A | 5/1997 | Dann |
| 5,685,870 A | 11/1997 | Tanghoj |
| 5,752,944 A | 5/1998 | Dann et al. |
| 6,010,489 A | 1/2000 | Blackburn |
| 6,059,762 A | 5/2000 | Boyer et al. |

*Primary Examiner*—John J. Calvert
*Assistant Examiner*—Angela J Grayson
(74) *Attorney, Agent, or Firm*—Schwartz Law Firm, P.C.

(57) ABSTRACT

A male incontinence device includes a receptacle formed of a shape-retaining material, and having a first open end adapted for receiving the penis of a user and a second end defining a urine discharge port. The discharge port is adapted for being located forward of the penis. A back flow chamber is formed with an interior of the receptacle, and is adapted for capturing urine flowing backward towards the user and away from the discharge port. A collection bag has a mouth communicating with the discharge port for collecting urine discharged through the receptacle. A support harness is adapted for being worn by the user to support the receptacle in an operative position during use.

18 Claims, 4 Drawing Sheets

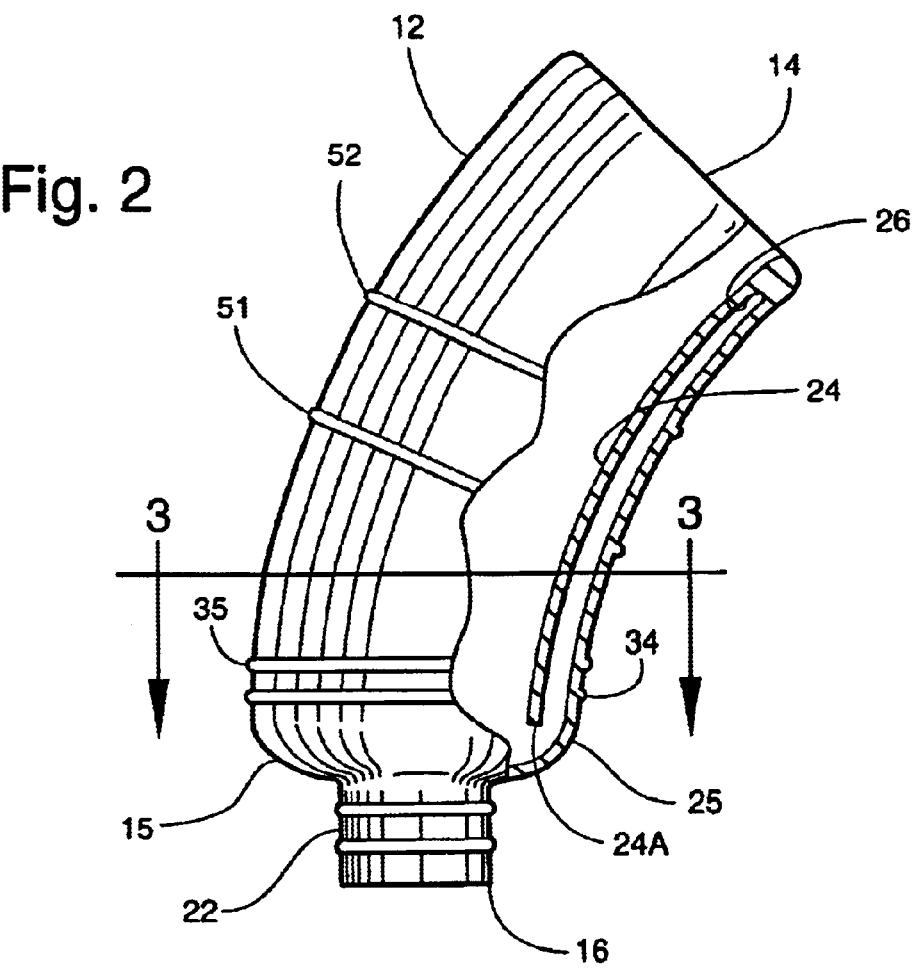
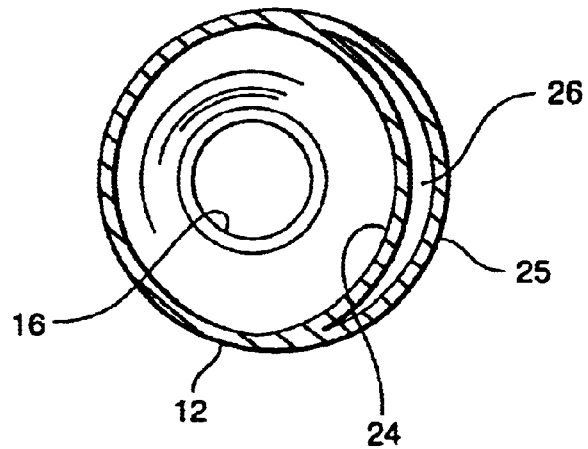

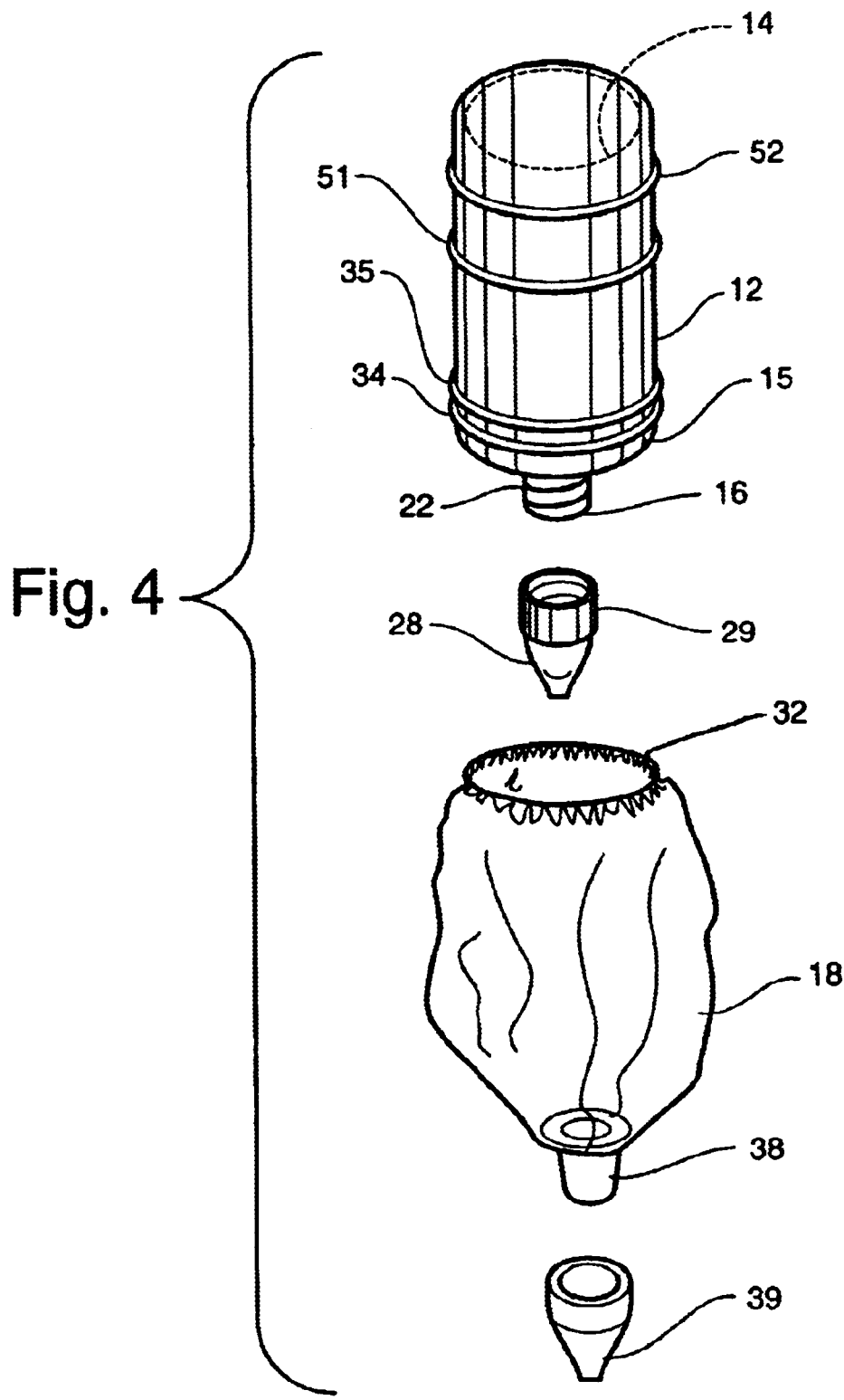

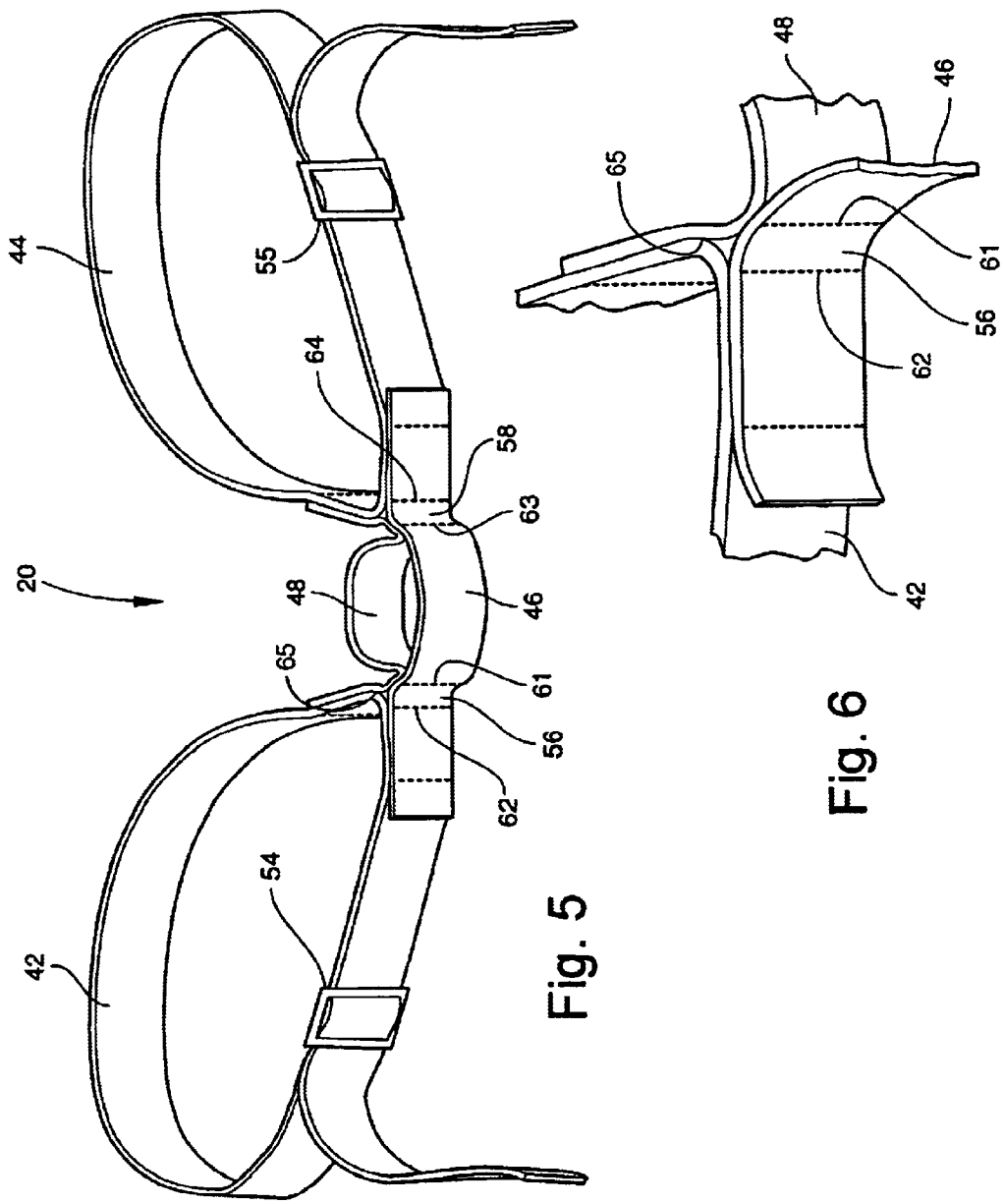

MALE INCONTINENCE DEVICE

This application claims priority to provisional patent application serial No. 60/217,434 filed on Jul. 10, 2000.

TECHNICAL FIELD AND BACKGROUND OF THE INVENTION

This invention relates to a male incontinence device. The invention fits securely and comfortably on the user without adhesives, tape, glue, or other constricting elements which may irritate and injure the skin. The invention is relatively inconspicuous under clothing, and provides a freedom of movement often sacrificed with commercially available male incontinence devices and catheters. Users can wear the present invention with confidence and without a feeling of self-consciousness.

Incontinence is a growing problem, particularly in those adults ages 65 and older. Approximately two million males in the United States suffer moderate to severe incontinence. Common causes for this condition include an enlarged prostate, prostate cancer, pelvic trauma, spinal cord injury, and medication side-effects. Over $16 billion is spent annually on incontinence related care.

The present invention addresses the limitations of certain prior art devices and catheters used for managing male incontinence. Specifically, the invention provides a "comfort wear" external device that is both effective and easy to use, and which resides generally unnoticed inside the clothing of the wearer without creating a feeling of self-consciousness. The invention is also applicable for monitoring the amount of urine expelled by patients in bladder training following prostate surgery, or radiation treatments. While not a cure for male urinary incontinence, the invention is intended to allow for a better quality of life with less skin irritation and fewer problems as compared to present, commercially available and accepted incontinent devices.

SUMMARY OF THE INVENTION

Therefore, it is an object of the invention to provide a male incontinence device which is effective and comfortable to wear.

It is another object of the invention to provide a male incontinence device which is non-irritating to the skin, and which does not use adhesives, tape, glue or other constricting elements attached directly to the penis.

It is another object of the invention to provide a male incontinence device which is easy to maintain and clean.

It is another object of the invention to provide a male incontinence device which includes a disposable urine collector, or alternatively, a reusable collector.

It is another object of the invention to provide a male incontinence device which has an ergonomic design for increased comfort.

It is another object of the invention to provide a male incontinence device which allows urine to be expelled from the bladder in a normal manner without removing the device from the user.

It is another object of the invention to provide a male incontinence device which is easily concealed under clothing.

It is another object of the invention to provide a male incontinence device which is adjustable to fit any user.

It is another object of the invention to provide a male incontinence device which is relatively easy to put on and remove.

It is another object of the invention to provide a male incontinence device which is especially designed for active adults.

It is another object of the invention to provide a male incontinence device which is designed for all day wear without changing.

It is another object of the invention to provide a male incontinence device which can be readily disassembled for cleaning and parts replacement, if necessary.

It is another object of the invention to provide a male incontinence device which allows air circulation between the receptacle and penis of the wearer.

These and other objects of the present invention are achieved in the preferred embodiments disclosed below by providing a male incontinence device including a receptacle formed of a shape-retaining material, and having a first open end adapted for receiving the penis of a user and a second end defining a urine discharge port. The discharge port is adapted for being located forward of the penis when the device is worn by the user. A back flow chamber is formed with an interior of the receptacle, and is adapted for capturing urine flowing backward towards the user and away from the discharge port during temporary above-horizontal positions. A collection bag has a mouth communicating with the discharge port for collecting urine discharged through the receptacle. A support harness is adapted for being worn by the user to support the receptacle in an operative position during use.

According to another preferred embodiment of the invention, the receptacle has an arcuate, ergonomic design.

According to another preferred embodiment of the invention, the support harness includes first and second leg straps adapted for being worn around the legs of the user.

According to another preferred embodiment of the invention, the leg straps of the harness are adjustable.

According to another preferred embodiment of the invention, the support harness further includes a receptacle support strap attached between the leg straps and defining an opening for receiving the receptacle.

According to another preferred embodiment of the invention, flex areas are formed at respective ends of the receptacle support strap. The flex areas are adapted to accommodate movement of the leg straps without substantial movement of the receptacle support strap.

According to another preferred embodiment of the invention, the flex areas are defined by respective pairs of spaced apart stitch lines.

According to another preferred embodiment of the invention, the receptacle is frictionally secured in position by the receptacle support strap of the support harness.

According to another preferred embodiment of the invention, first and second spaced positioning ribs are formed around an exterior of the receptacle for positioning the receptacle support strap therebetween.

According to another preferred embodiment of the invention, the receptacle is formed of a rigid material.

According to another preferred embodiment of the invention, the receptacle is formed of a semi-rigid material.

According to another preferred embodiment of the invention, the mouth of the collection bag includes an elastic ring for securing the bag to the receptacle.

According to another preferred embodiment of the invention, first and second spaced positioning ribs are formed around an exterior of said receptacle and adjacent the discharge port for positioning the elastic ring of the collection bag on the receptacle.

According to another preferred embodiment of the invention, the collection bag has a drain outlet located opposite the mouth, and a removable cap for opening and closing the drain outlet.

According to another preferred embodiment of the invention, a one-way valve is located at the discharge port of the receptacle for providing one-way flow of urine outwardly from the receptacle and into the collection bag.

BRIEF DESCRIPTION OF THE DRAWINGS

Some of the objects of the invention have been set forth above. Other objects and advantages of the invention will appear as the description proceeds when taken in conjunction with the following drawings, in which:

FIG. 2 is a side elevation of the receptacle with a portion of the receptacle wall broken away to illustrate the construction of the interior back flow chamber;

FIG. 3 is a cross-sectional view taken substantially along line 3—3 of FIG. 2;

FIG. 4 is a perspective view of the receptacle and urine collection bag with removable elements disassembled and pulled apart;

FIG. 5 is a perspective view of the support harness with the receptacle and collection bag removed; and FIG. 6 is an enlarged, fragmentary perspective view of the support harness and showing one of the flex areas in greater detail.

DESCRIPTION OF THE PREFERRED EMBODIMENT AND BEST MODE

Figure 1:
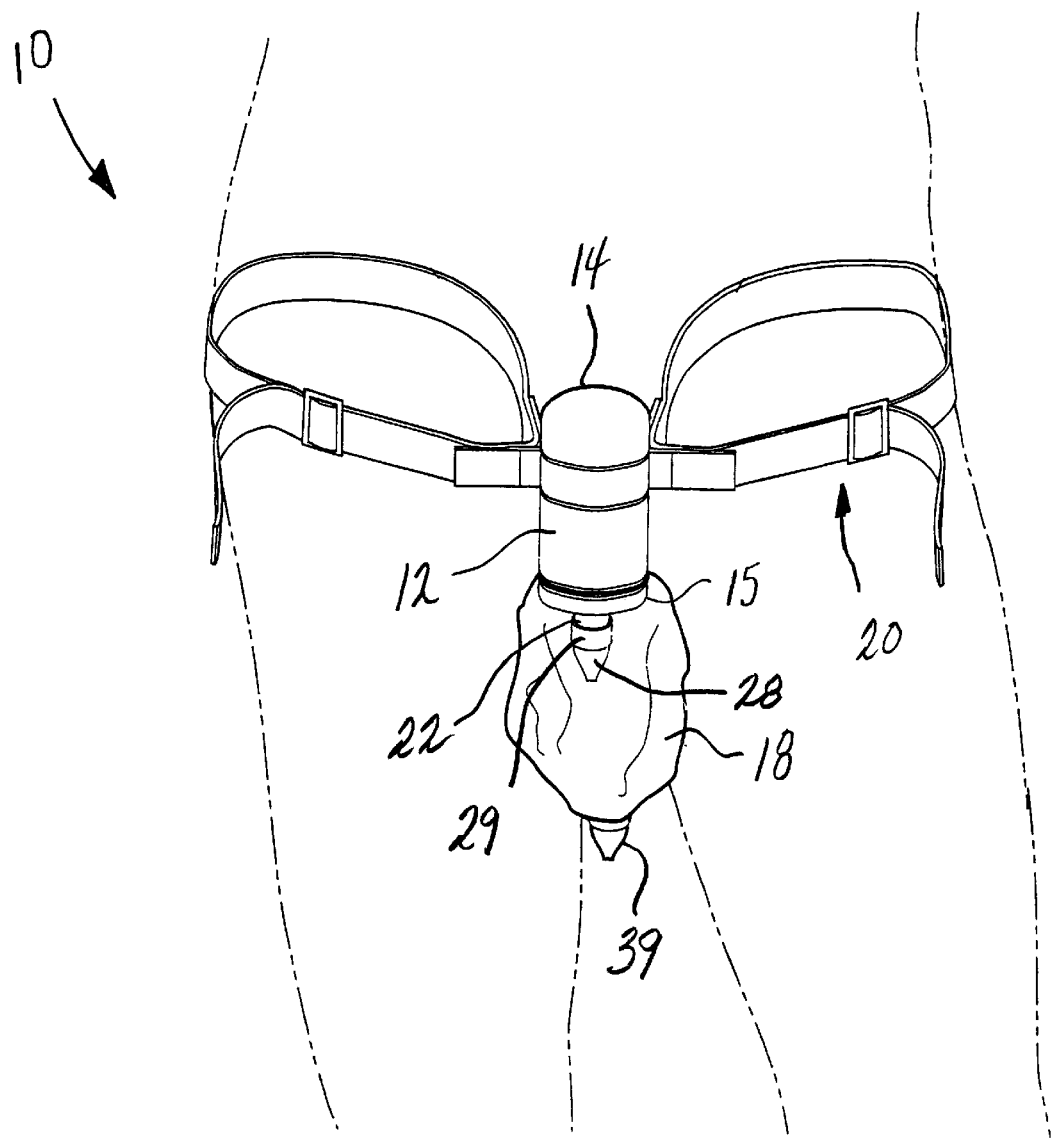
FIG. 1 is an environmental perspective view of a male incontinence device according to one preferred embodiment of the invention, and illustrating the device being worn by a user shown in phantom.

Referring now specifically to the drawings, a male incontinence device according to the present invention is illustrated in FIG. 1 and shown generally at reference numeral 10. The device 10 is intended for use by males suffering from moderate to severe incontinence. The device includes a hollow receptacle 12 having a first open end 14 adapted for receiving the penis of the user and a second end 15 defining a urine discharge port 16. A urine collection bag 18 is attached to the receptacle 12 over the discharge port 16 to collect urine discharged by the user during wear. A removable support harness 20 is worn around the upper thighs of the user, and is designed to support the receptacle 12 in an operative position over the penis. Each of the receptacle 12, urine collection bag 18, and support harness 20 is described in further detail below.

Referring to FIGS. 1, 2, and 3, the receptacle 12 is formed of a shape-retaining material, such as a thin rigid or semi-rigid molded plastic, which does not form or adhere directly to the penis during use. The term "rigid" is defined herein as resisting change in form under a pressure of at least 10 pounds. The term "semi-rigid" is defined as resisting a change in form under a pressure of at least 1 pound. Preferably, the receptacle 12 has an arcuate, ergonomic design intended to conform to the natural anatomy of the body and penis. The first open end 14 of the receptacle 12 is relatively large to promote air circulation between the penis and interior of the receptacle. The discharge port 16 at the second end 15 of the receptacle 12 is defined by an elongated, threaded neck 22.

As shown in FIGS. 2 and 3, a chamber wall 24 is formed inside the receptacle 12 and cooperates with the receptacle wall 25 to define a back flow chamber 26. The leading edge 24A of the chamber wall 24 is spaced from the receptacle wall 25 to form an inlet sufficient for receiving into the chamber 26 urine running backward from the discharge port 16 and towards the user. The inlet is designed to capture any urine leaked by the user while the device 10 is not in a near vertical or downwardly angled position. When the device 10 is returned to a more vertical position, any urine contained in the back flow chamber 26 will drain outwardly from the receptacle 12 through the discharge port 16 in the usual manner. Drainage through the discharge port 16 occurs even when in a sitting position with the legs slightly open. As a further measure of protection and comfort, the top inside portion of the receptacle 12 may be lined with a soft non-absorbent material (not shown).

Referring to FIGS. 1 and 4, in order to prevent the inflow of urine from the collection bag 18 into the receptacle 12, a one-way valve 28, such as a flutter, reed, or duck bill valve, is applied to the receptacle 12 at the discharge port 16. The valve 28 includes an internally-threaded attachment cap 29 which is conveniently screwed on and off of the threaded neck 22 of the receptacle 12.

The collection bag 18 fits over the second end 15 of the receptacle 12 to cover the valve 28 and threaded neck 22. Preferably, the mouth at the top end of the bag 18 includes an elastic ring 32, shown in FIG. 4, which is positioned between spaced ribs 34 and 35 formed with the receptacle 12. The elastic ring 32 securely attaches the bag 18 to the receptacle 12, and creates a seal sufficient to prevent any leakage of urine outwardly from the bag 18. Importantly, the collection bag 18 is not strapped directly to the leg of the user, but instead can shift freely within the pants of the user without pulling or tugging on the penis. The collection bag 18 may be formed in any desired shape and size, and may be either disposable or reusable. Preferably, the bag 18 does not have any sharp edges which can irritate the skin of the user. According to one embodiment, the bag 18 is constructed of a polymer or copolymer material designed to contain between 250–300 ml of urine. The bag 18 has an oblong oval shape with an approximate width of 10 cm and length of 12 cm.

A drain outlet 38 is formed in a bottom end of the bag 18 such that the user is able to urinate through the bag 18 in a normal manner without first removing the receptacle 12. A convenient press-on cap 39 is provided to open and close the drain outlet 38.

Referring to FIGS. 1, 5, and 6, the support harness 20 is worn around the upper thighs of the user, and includes first and second adjustable, elastic leg straps 42 and 44 and a pair of elastic receptacle support straps 46 and 48. The receptacle support straps 46, 48 interconnect the leg straps 42, 44 and define an opening sufficient to receive and frictionally secure the receptacle 12 to the harness 20. Preferably, the receptacle 12 includes spaced positioning ribs 51 and 52 for properly positioning and retaining the straps 46, 48 on the receptacle 12. A thin rubber inlay (not shown) may also be included on the inside of the straps 42, 44, 46, and 48 for increased holding strength. The harness 20 is worn on the user to locate the receptacle 12 in the operative position shown in FIG. 1. Each of the leg straps 42 and 44 preferably includes an adjustment frame 54 and 55 for allowing size adjustment of the leg openings to fit the particular user. As best shown in FIGS. 5 and 6, flex areas 56 and 58 are formed at respective ends of the receptacle straps 46 and 48 adjacent the receptacle opening in order to accommodate movement of the leg straps 42 and 44 without substantial corresponding movement of the receptacle straps 46, 48 and receptacle 12. The flex areas 56 and 58 are defined by respective pairs of spaced stitch lines 61, 62 and 63, 64 located on either side of the receptacle opening. FIG. 6 illustrates the flex area 56 in greater detail. Stitch line 61 extends through the two receptacle support straps 46 and 48 to form one end closure for the receptacle opening. Stitch line 62 extends through the receptacle strap 46 and leg strap 42. A corresponding stitch line (not shown) extends through the other receptacle strap 48 and leg strap 42 at point 65. The other flex area 58 is formed in an identical manner. The flex areas 56 and 58 cooperate during activity of the user to promote comfort and provide an increased freedom of movement.

In an alternative embodiment of the male incontinence device, the elastic leg straps of the harness are formed in various sizes without any particular adjustment means. In a further alternative embodiment, the support harness may be incorporated into a pair of conventional-looking mens briefs or boxers.

A male incontinence device is described above. Various details of the invention may be changed without departing from its scope. Furthermore, the foregoing description of the preferred embodiment of the invention and the best mode of practicing the invention are provided for the purpose of illustration only and not for the purpose of limitation—the invention being defined by the claims.

I claim:

1. A male incontinence device, comprising:
   (a) a tubular walled receptacle formed of a shape-retaining material, and having a first open end adapted for receiving the penis of a user and a second end defining a urine discharge port, said discharge port adapted for being located forward of the penis;
   (b) a chamber wall located adjacent an interior of the receptacle wall and cooperating with said receptacle to form a back flow chamber adapted for capturing urine flowing backward towards the user and away from said discharge port; and
   (c) a collection bag having a mouth communicating with said discharge port for collecting urine discharged through said receptacle.

2. A male incontinence device according to claim 1, wherein said receptacle has an arcuate, ergonomic design.

3. A male incontinence device according to claim 1, and comprising a support harness including first and second leg straps adapted for being worn around the legs of the user.

4. A male incontinence device according to claim 3, wherein the leg straps of said support harness are adjustable.

5. A male incontinence device according to claim 3, wherein said support harness further comprises a receptacle support strap attached between said leg straps and defining an opening for receiving said receptacle.

6. A male incontinence device according to claim 5, and comprising flex areas formed at respective ends of the receptacle support strap, said flex areas being adapted to accommodate movement of the leg straps without substantial movement of the receptacle support strap.

7. A male incontinence device according to claim 6, wherein said flex areas are defined by respective pairs of spaced apart stitch lines.

8. A male incontinence device according to claim 5, wherein said receptacle is frictionally secured in position by the receptacle support strap of said support harness.

9. A male incontinence device according to claim 5, and comprising first and second spaced positioning ribs formed around an exterior of said receptacle for positioning said receptacle support strap therebetween.

10. A male incontinence device according to claim 1, wherein said receptacle is formed of a rigid material.

11. A male incontinence device according to claim 1, wherein said receptacle is formed of a semi-rigid material.

12. A male incontinence device according to claim 1, wherein the mouth of said collection bag includes an elastic ring for securing said bag to said receptacle.

13. A male incontinence device according to claim 12, and comprising first and second spaced positioning ribs formed around an exterior of said receptacle and adjacent the discharge port for positioning the elastic ring of said collection bag on said receptacle.

14. A male incontinence device according to claim 1, wherein said collection bag comprises a drain outlet located opposite the mouth, and a removable cap for opening and closing the drain outlet.

15. A male incontinence device according to claim 1, and comprising a one-way valve located at the discharge port of said receptacle for providing one-way flow of urine outwardly from said receptacle and into said collection bag.

16. A male incontinence device, comprising:
   (a) a tubular walled receptacle formed of a shape-retaining material having an arcuate ergonomic design, and a first open end adapted for receiving the penis of a user and a second end defining a urine discharge port, said discharge port adapted for being located forward of the penis;
   (b) a chamber wall located adjacent an interior of the receptacle wall and cooperating with said receptacle to form a back flow chamber adapted for capturing misdirected urine flowing backward towards the user and away from said discharge port;
   (c) a one-way valve located at said discharge port for controlling the flow of urine outwardly from said receptacle; and
   (d) a collection bag having a mouth extending over the one-way valve at said discharge port, said collection bag being adapted for collecting urine discharged through said receptacle.

17. A male incontinence device, comprising:
   (a) a tubular walled receptacle formed of a shape-retaining material, and having a first open end adapted for receiving the penis of a user and a second end defining a urine discharge port, said discharge port adapted for being located forward of the penis;
   (b) a chamber wall located adjacent an interior of the receptacle wall and cooperating with said receptacle to form a back flow chamber adapted for capturing urine flowing backward towards the user and away from said discharge port;
   (c) a collection bag having a mouth communicating with said discharge port for collecting urine discharged through said receptacle; and
   (d) means for supporting said receptacle in an operative position during use.

18. A male incontinence device, comprising:
   (a) a tubular walled receptacle formed of a rigid material having an arcuate ergonomic design, and a first open end adapted for receiving the penis of a user and a second end defining a urine discharge port, said discharge port adapted for being located forward of the penis;
   (b) a chamber wall located adjacent an interior of the receptacle wall and cooperating with said receptacle to form a back flow chamber adapted for capturing urine flowing backward towards the user and away from said discharge port;
   (c) a collection bag having a mouth communicating with said discharge port for collecting urine discharged through said receptacle; and
   (d) means for supporting said receptacle in an operative position during use.

* * * * *